United States Patent [19]

Gordon

[11] Patent Number: 5,087,438

[45] Date of Patent: * Feb. 11, 1992

[54] METHOD FOR AFFECTING INTRACELLULAR AND EXTRACELLULAR ELECTRIC AND MAGNETIC DIPOLES

[76] Inventor: Robert T. Gordon, 4936 W. Estes, Skokie, Ill. 60077

[*] Notice: The portion of the term of this patent subsequent to Aug. 30, 2005 has been disclaimed.

[21] Appl. No.: 221,991

[22] Filed: Jul. 20, 1988

Related U.S. Application Data

[63] Continuation-in-part of Ser. No. 627,536, Jul. 3, 1984, Pat. No. 4,767,611.

[51] Int. Cl.⁵ ............................................. A61K 49/00
[52] U.S. Cl. ................................. 424/9; 128/653.1; 128/654; 600/9; 600/10
[58] Field of Search ............... 424/9; 128/1, 3, 653, 128/660

[56] References Cited

U.S. PATENT DOCUMENTS

| | | | |
|---|---|---|---|
| 4,106,488 | 8/1978 | Gordon | 424/85 |
| 4,136,683 | 1/1979 | Gordon | 128/1.3 |
| 4,359,453 | 11/1982 | Gordon | 424/9 |
| 4,452,773 | 6/1984 | Molday | 424/1.1 |
| 4,508,625 | 4/1985 | Graham | 210/695 |
| 4,577,636 | 3/1986 | Spears | 128/654 |
| 4,615,879 | 10/1986 | Runge et al. | 424/9 |

Primary Examiner—Robert A. Wax
Assistant Examiner—F. Tsung
Attorney, Agent, or Firm—Scully, Scott, Murphy & Presser

[57] ABSTRACT

A treatment of infectious diseases and enhancement of genetic engineering processes is described comprising the use of external electromagnetic energy to alter electric and magnetic dipoles intracellularly.

The process comprises introducing minute particles into the interior of cells in a host organism. These particles are capable of affecting the intracellular conductivity, dielectric properties, dipole content and membrane characteristics of the cell and nucleus. The particles are introduced intravenously, intra-arterially, and/or intra-lymphatically and the organism is then exposed to an alternating electromagnetic field to introduce energy into the cells.

19 Claims, 4 Drawing Sheets

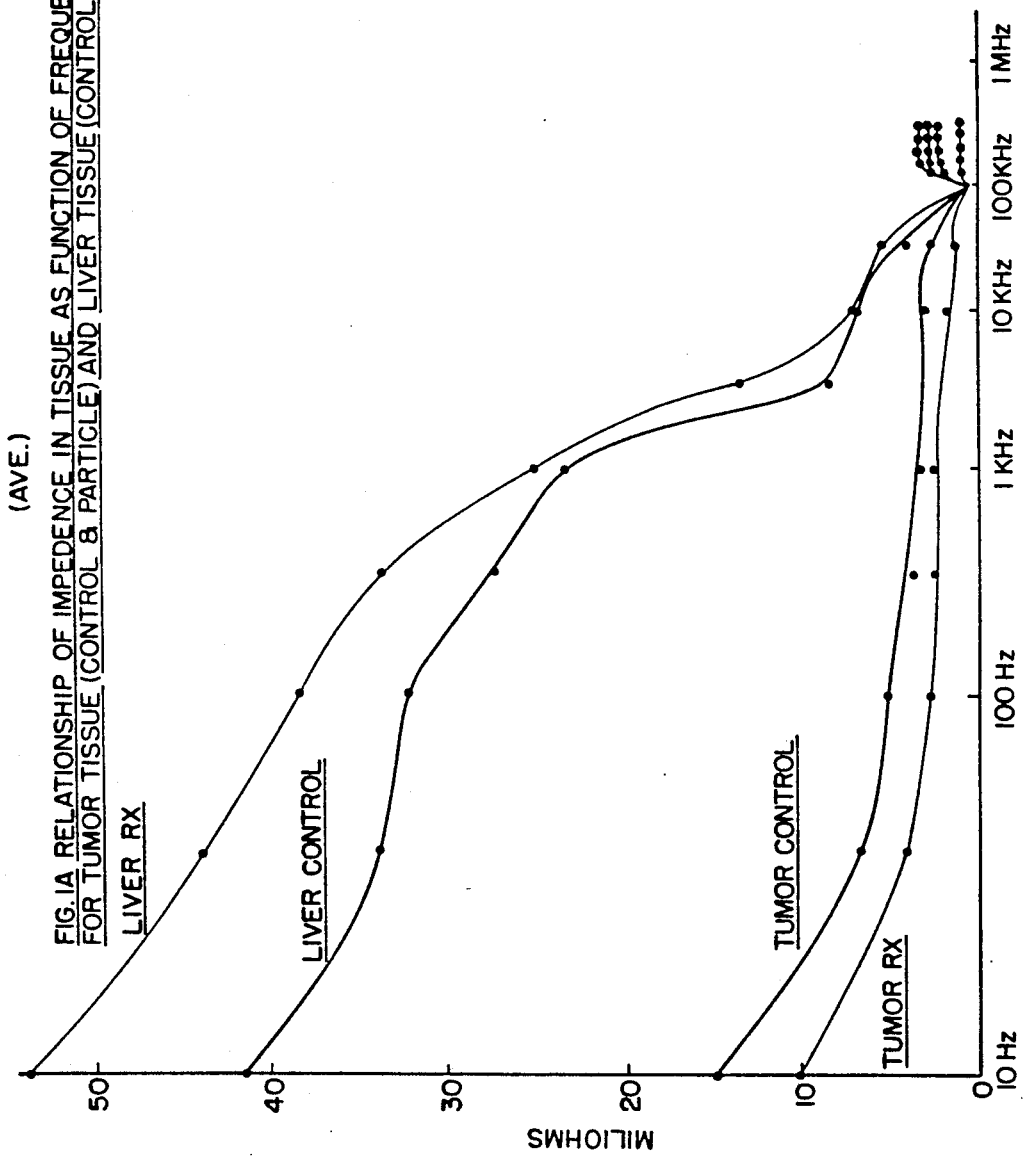

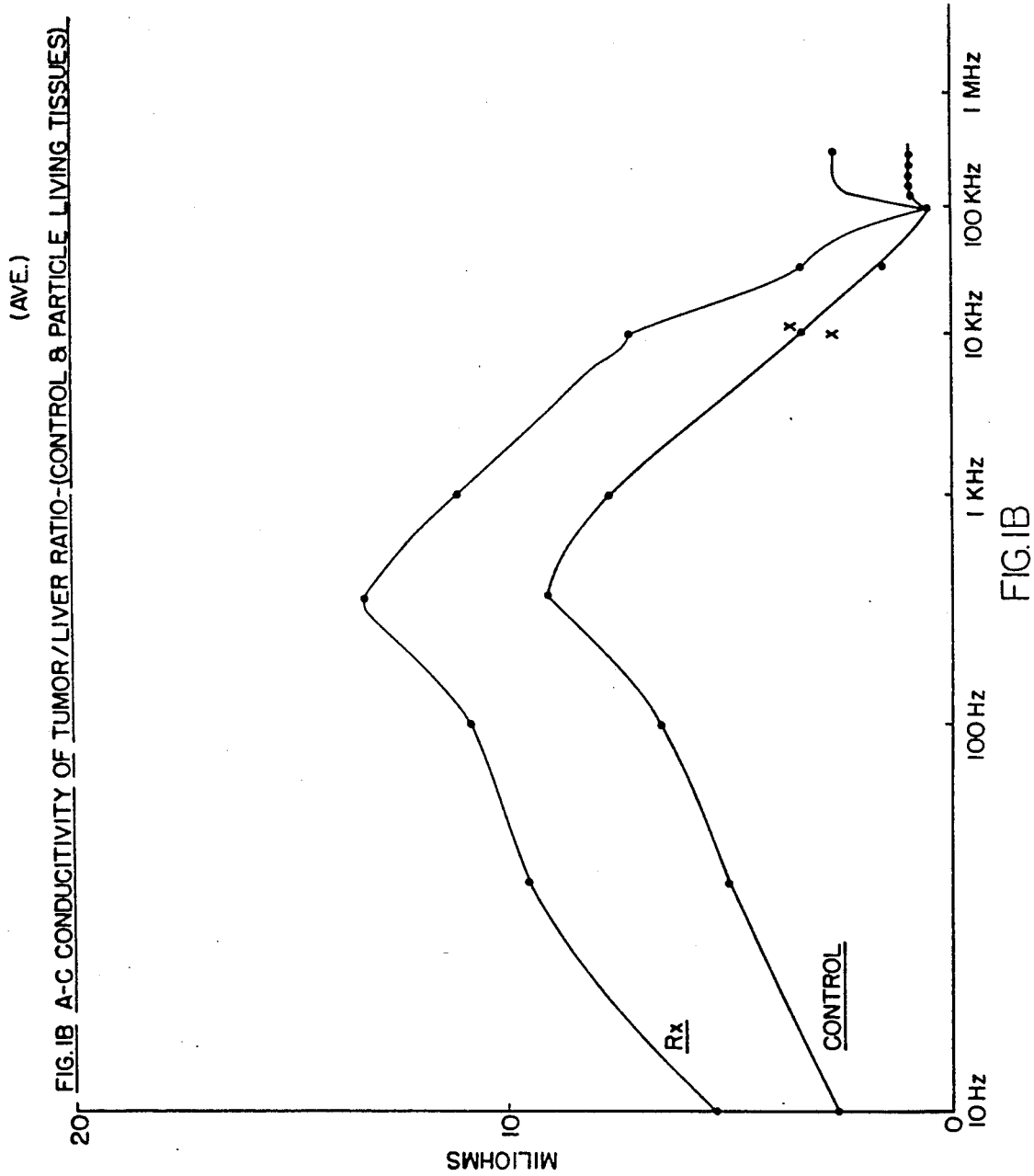

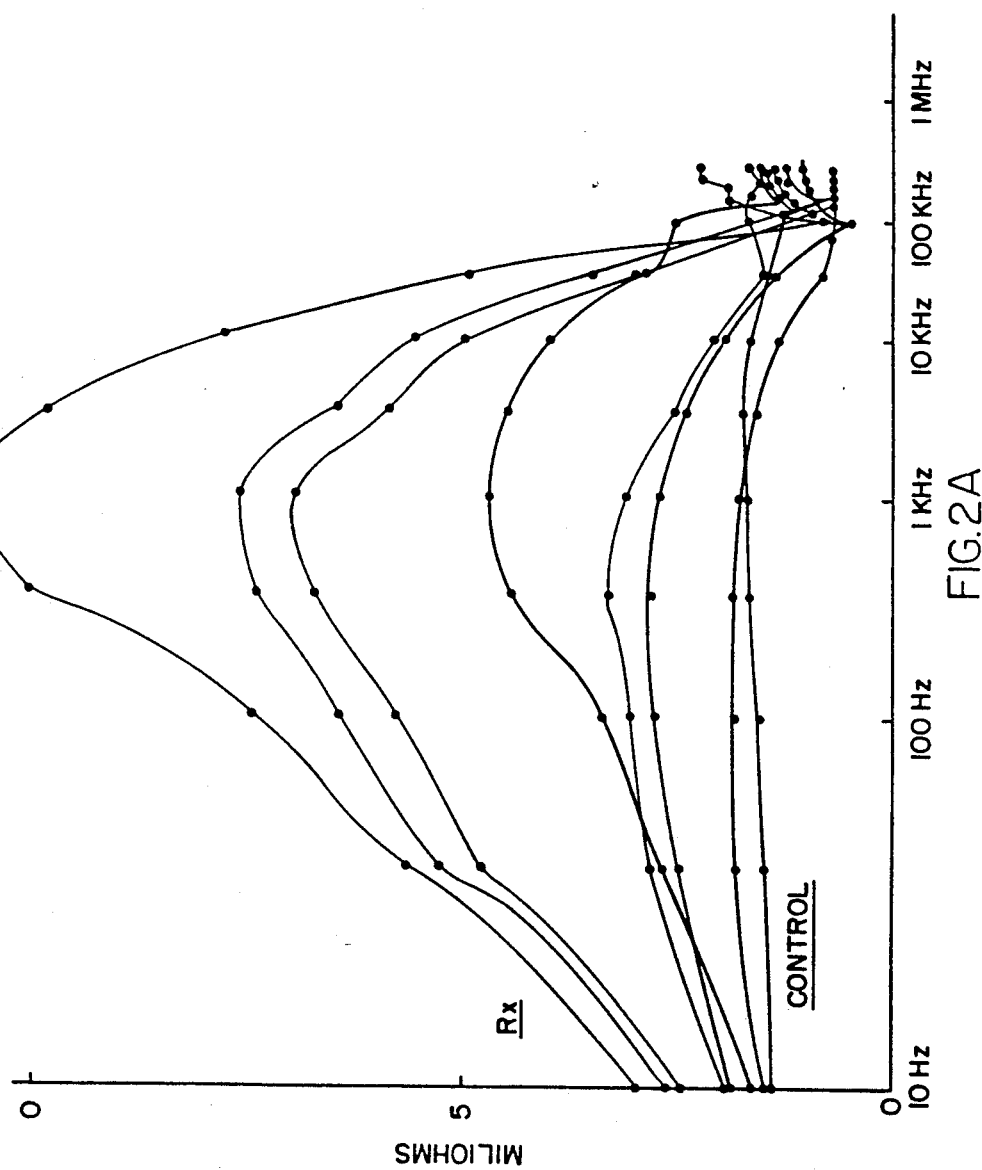

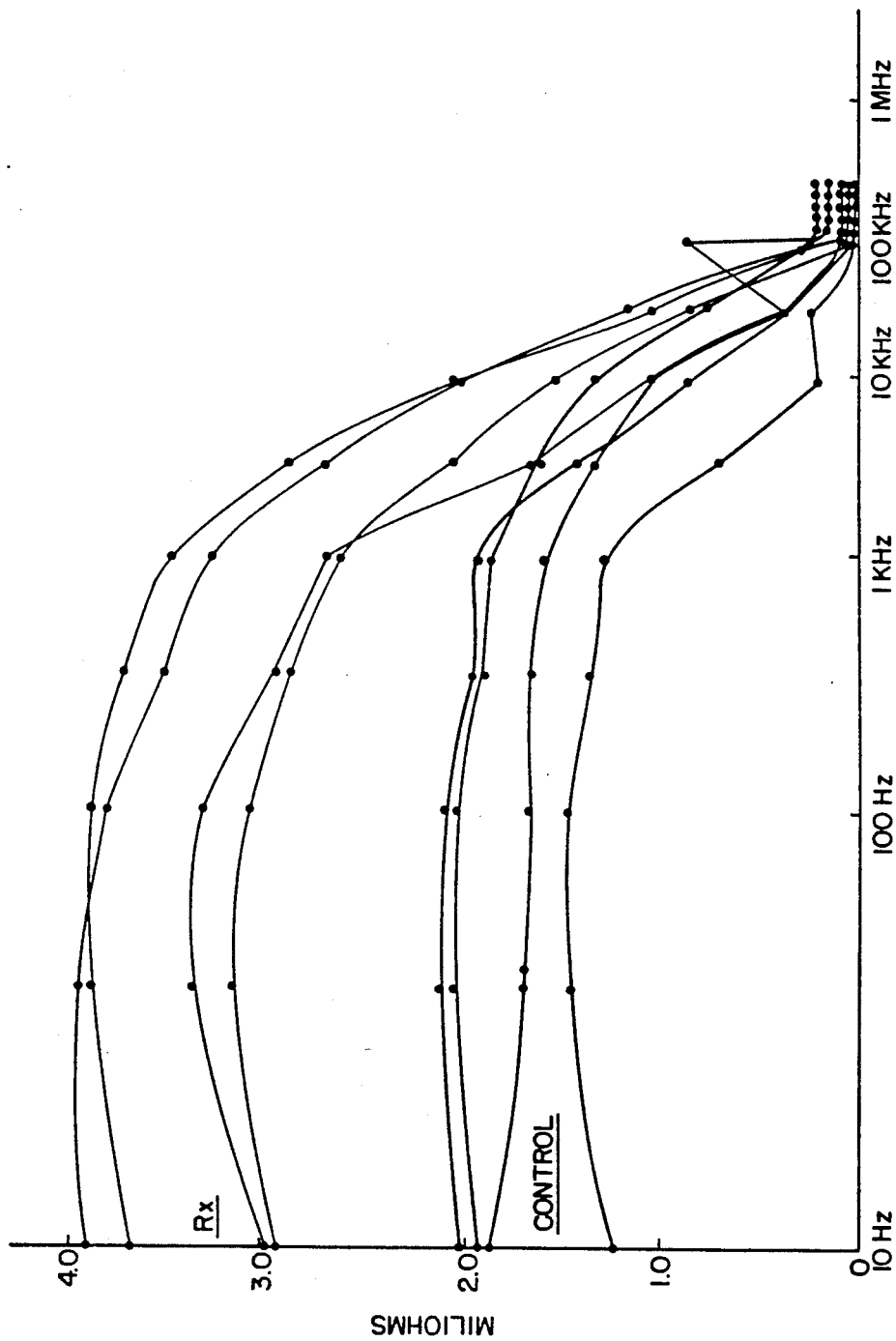

METHOD FOR AFFECTING INTRACELLULAR AND EXTRACELLULAR ELECTRIC AND MAGNETIC DIPOLES

FIELD OF THE INVENTION

This application is a continuation-in-part of U.S. patent application Ser. No. 627,536 filed July 3, 1984 and now U.S. Pat. No. 4,767,611.

This invention relates to the field for affecting intracellular and extracellular electric and magnetic dipoles and more specifically to a method for affecting intracellular and extracellular electric and magnetic dipoles for use in the treatment of cancer and other diseases, including infectious diseases.

BACKGROUND OF THE INVENTION

The increased sensitivity of cancer cells as compared to normal cells to increased temperature has been noted for some time. Cancer cells, because of their higher rate of metabolism, have higher resting temperatures compared to normal cells. The normal resting temperature of the cancer cell is known to be 37.5° Centigrade, while that of the normal cell is 37° Centigrade. Another physical characteristic that differentiates the cancer cells from the normal cells is that cancer cells die at lower temperatures than do normal cells. The temperature at which a normal cell will be killed and thereby irreversibly will be unable to perform normal cell functions is a temperature of 46.5° Centigrade) on the average. The cancer cell, in contrast, will be killed at the lower temperature of 45.5.° Centigrade. The temperature elevation increment necessary to cause death in the cancer cell is determined to be at least approximately 8.0° Centigrade, while the normal cell can withstand a temperature increase of at least 9.5° Centigrade.

In attempts to solve the existing problem as to how to get energy into the cancer cells without affecting the normal cells, efforts have been made to couple electromagnetic fields extracellularly to tissues to attempt to induce heating. However, these efforts have not been effective largely because of the inability to differentiate the cancer cells form the normal cells.

The electromagnetic field interacts with tissue in several ways There are displacement currents due to the drift of electrons, polarization of atoms or molecules to produce dipoles and the interaction with dipoles already present. The coupling of electromagnetic energy to the tissue depends on the electrical conductivity ($\sigma$) and the dielectric constant ($\epsilon$). The power imparted to the tissue depends on the square of the amplitude of the field and the coupling constant to the tissue. The dielectric properties of the material depend on its composition and structure (i.e ions, polar molecules, etc.).

In general:

$$\epsilon = \epsilon' - j\epsilon''$$

where $\epsilon'$ = real component related to energy stored in the material in electric fields $\epsilon\Delta$ = imaginary component related to loss in the form of heat =

$$\frac{\sigma}{2\pi f \epsilon_0}$$

$\sigma$ = conductivity so that conductivity is related to the amount of heat loss Often as there is an increase in frequency, $\epsilon'$ decreases due to less ordering and $\epsilon''$ increases.

In tissue a plot of the dielectric constant as a function of frequency often shows three dispersions. Each dispersion is related to a specific phenomenon. The $\alpha$ dispersion (at $\approx$ 80–100 Hz) is due to the interaction of the charges on the cell surface with the ions in solution and the impedance if the membrane system.

The $\beta$ dispersion (at $\approx$ 50 KHz) is related to the cell membrane's insulation of the $H_2O$. Above 10 GHz the $\gamma$ dispersion is due to the $H_2O$ and electrolyte solution. To overcome these problems the common practice is to use a frequency >> 1 KHz to short out the membrane effects and to deliver energy to the cytoplasm.

Consequently, frequencies greater than 1 KHz and usually greater than 1 MHz are utilized to overcome problems with the cell membrane and deliver energy to the cell. Traditionally, frequencies of 13 MHz or 2450 MHz are used. However, the problem remains that at these high frequencies not only are the cancer cells affected but the normal cells are also affected and consequently one is limited in the amount of energy which can be delivered to the cancer cells.

The present invention seeks to overcome this problem, by modifying the intracellular environment to allow the use of lower frequencies if possible and to enhance the effect in the cancer cells without affecting the normal cells.

BRIEF DESCRIPTION OF THE DRAWINGS

FIG. 1A: Illustrates the measurements of impedance in tissue as a function of frequency for Tumor tissue (control and treated) and Liver tissue (control and treated).

FIG. 1B: Demonstrates the A-C conductivity Tumor/Liver ratio (control and particle living tissue) as a function of frequency.

FIG. 2A: Illustrates the A-C conductivity ratio Tumor/Liver (control and particle containing tissue) in a second series of animals as a function of frequency.

FIG. 2B: Illustrates the difference in impedance between the Tumor and the Liver in the treated animals as compared to the Control animals as a function of frequency.

OBJECT OF THE INVENTION

The present invention comprises the introduction of minute particles into cells of a host organism to alter the intracellular environment and to enhance the effect of external electromagnetic energy on the cells consequently affecting the cells without affecting the normal cells.

DESCRIPTION OF THE INVENTION

The use of particles to alter the energy level in the cell by the absorption of electromagnetic energy by the particle has been disclosed by the applicant in his U.S. Pat. Nos. 4,106,488; 4,136,683; 4,303,636; and 4,359,453. The present invention seeks to use particles to affect the absorption of energy by the cell itself in response to an external alternating electromagnetic field. The implementation of this present treatment method in part utilizes inventive aspects which are the subject of other applications for U.S. Letters Patent by the same inventor as recited- hereinafter. For example, a fuller understanding of the technology underlying the Gordon treatment reveals the operation of subtle mechanisms which can themselves become a contributing factor in the course of treatment and are incorporated herein by reference. The selection of particle compositions for use in this present invention as disclosed in the applicant's above described U.S. Patents and as disclosed in co-pending and commonly assigned applications Ser. Nos. 418,298; 464,870 including C.I.P; 522,941 including C.I.P. 535,390; 524,844; and 561,811 of the same inventor, are incorporated herein by reference.

Below several MHz the transmission of energy directly to the cell by an external alternating electromagnetic field is affected by the characteristics of the cell membrane. The charge accumulation on the membrane from intracellular and extracellular fluids accounts for the dielectric polarization of the membrane. The intracellular and extracellular electrolyte solution accounts for the conductance.

In the prior Robert T. Gordon U.S. Pat. Nos. 4,303,636; 4,106,488 and 4,359,455, a high frequency magnetic field is employed to have a direct effect on the particles so that diseased tissue can be killed by thermal effects due to hysteresis loss form the particles themselves when the field is relaxed In contrast to this phenomena, the particles of the present invention are employed to alter the environment such as the magnetic dipoles charge accumulation and conductivity both intra and extra cellularly of a host organism.

The altered environment in turn produces thermal effects (an increase in temperature) when subjected to an alternating magnetic field at relatively low frequencies. These thermal effects are not due to a hysteresis loss from the particles. The frequency range employed according to the present invention which is lower than that of the aforesaid Gordon patents thereby reduces the power requirements. The design and timing of treatment will differ because of the lower frequency ranges employed in the treatment methods of the present invention. One of the additional advantages of the present invention resides in the fact that coil apparatus does not have to be used as was the case in the Gordon patents noted above, the instant invention capable of being practiced inter alia with capacitor plates for developing the frequencies required for treatment.

In the Gordon patents noted above, optimum results were obtained by the metabolism of the particles by the cells. In the present invention effective treatment may be obtained outside the cell environment since the membrane surface dipoles are affected by the particles. The present invention, however, also applies to affecting the dielectric, conductivity and frequency dependent dispersion curves both extra cellularly as well as intra cellularly (i.e., those instances where the particles are metabolized or absorbed by the cells of a host organism whether the cells are diseased cells or normal cells).

Through the introduction of particles in the cancer cells the intracellular conductivity can be altered as well as the charge accumulation on the cell membrane This enhancement of conductivity as well as the alteration in membrane events allows two benefits The alteration in cell membrane characteristics enables the delivery of energy intracellularly at a lower frequency due to the effect on the charge accumulation on the cell membrane. The increased conductivity of the cell allows more energy to be delivered and a better coupling at the given frequency.

In addition, the effect on the normal cells is greatly reduced because the energy requirements are less, the normal cell membrane still acts as a barrier at this frequency and the frequency to be utilized can be lowered.

Consequently, through the alteration of the intracellular environment and the membrane effects at a given frequency, more energy can be delivered to the cancer cells, a lower frequency can be utilized since the cancer cell membrane will start to short out at a lower frequency and the effect on the normal cells is reduced due to its intact cell membrane characteristics.

EXAMPLES

In this original study 12 Sprague-Dawley rats with spontaneous mammary tumors were utilized. Six of the animals were injected with 2 cc. of $FeTPPS_4$ Acetate in a dosage of 10 mg/cc. The animals were observed for any side effects and at 48 hours biopsies were performed of the tumor, liver, spleen, kidney, heart, and lung. These biopsies were performed on both the control and injected animals.

Measurements of conductivity were then performed at 37° C. in the living tissue of the dielectric properties by means of a Bonton Impedence measuring device and the status of the electric and magnetic dipoles. The results are reported in FIGS. 1A, 1B, 2A and 2B which illustrate the difference in dielectric properties between the treated and untreated tumor as compared to a normal organ such as the liver;

FIGS. 1A and 2B show the change in impedence with frequency for several tissues. The particle containing tumor tissue appears more conductive than the control tumor tissue or the liver tissue.

In the tumor containing the particles the conductivity increases as does the magnetic susceptibility (Gordon et al. in press). However, in the liver tissue due to differences in metabolism and processes of the particle, the conductivity decreases and the magnetic susceptibility decreases (Gordon et al. in press). This difference in processing of the particle system is designed to maximize the ability to differentially affect the tumor cells with minimal or no effect to the normal cells. Differences in processing of systems by different tissues is seen by the difference of fluorescence in the same amount of porphyrins in different tissues.

FIGS. 1B and 2A illustrates another aspect of the present invention. FIGS. 1B, and 2A show the plot of the conductivity ratio of Tumor/Liver of particle containing tissue versus control tissue. These studies were performed with living tissue having been injected intravenously with $FeTPPS_4$-acetate. The data suggests for this particle system a maximum at 500 Hz. However, at 10 Hz and also at 200 KHz-500 KHz the T/L conductivity for the particle containing tissue is 2× that of the normal tissue which can prove useful.

In addition, the ratio for particle containing tissue is higher at lower frequencies as suggested by the shift of the left hand hump of the particle containing curve to the left. This data supports the use of lower frequencies in the particle containing systems.

The dielectric properties and conductivity of materials are temperature dependent. The membrane charging time constant and frequency of dispersion often vary 2% per °C. The frequency dependent dispersion curves of materials vary with temperature. A further innovation of the instant invention is to utilize the dielectric properties, conductivity, and frequency dispersion curves of the living tissue to identify the temperature of that tissue and follow the treatment process.

The dielectric properties change with the metabolism rate in the cell and consequently measurement of these properties allows knowledge not only of the temperature but also the state of metabolism in the cell and allows a means of following changes in the state of metabolism.

Similar results are available from the other tissues studied and readily demonstrate the effect of the particles on the dielectric properties conductivity and electric dipoles of certain tissues and the differential between the tumor tissue and normal tissue.

As disclosed by the applicant in his U.S. Pat. No. 4,136,683 and as disclosed in copending and commonly assigned application Ser. No. 535,390 (C.I.P. to application Ser. No. 522,941) of the same inventor and incorporated herein by reference, this present invention can be used to create a three-dimensional temperature map of the body. In addition, the measurement of these properties allows one to follow the distribution of the particles in the body by following the change in the dielectric properties, conductivity, and frequency dispersion curves both before and after ingestion of the particles.

Molecules in a cell can be affected if $\mu E \geq kT$ (where $\mu$ is dipole moment, E is the field strength, k is the Boltzman constant, and T is absolute temperature). Consequently by introducing the particles and increasing the relative dipole moment in the cell the direct effects on molecules in the cell can be enhanced even beyond thermal effects. Therefore, this present invention may directly affect the molecules in the cell.

Through these processes the dielectric properties across the membrane can be affected including the stimulation and/or alteration of nerve impulses and/or electrical events.

The ionic environment around the surface of the particle by becoming polarized can produce increased dielectric properties as well. In addition, membrane effects with the anionic proteinaceious material which accumulates around the cell can produce local effects.

When you have a mixture with different dielectric properties relaxation phenomenon will occur not at a single frequency, but over a wide range of frequencies. The curve is broadened due to interactions in the mixture. Inclusion of material of low dielectric constant will lower the dielectric constant of the mixture. Therefore, the addition of particles to the inside of the cell broadens the frequency response of intracellular structures as compared to the other cells and structures. Particle geometry also affects the frequency response. Consequently, the presence of the particles allows for a differential affect on subcellular structures.

The choice of particle type, size and shape can be highly significant to effective treatment, particularly where subcellular localization or other subtle differentiations in metabolic activity, for example, are conveniently utilized to maximize particle uptake and absorption. Suitable particles and exemplifications of selection parameters are disclosed and examined in copending and commonly assigned application Ser. No. 535,390 of the same inventor, incorporated herein by reference.

The particles may be chosen from ferromagnetic, paramagnetic, or diamagnetic particles. The particle systems include metalloporphyrins, $Fe_2O_3$, metal-metalloporphyrins and particularly useful particles including both inorganic elements and compounds as well as metal containing organic compounds. Inorganic elements and compounds particularly well suited, owing to their favorable magnetic parameters, comprise elements such as dysprosium, erbium, europium, gadolinium, holmium, samarium, terbium, thulium, ytterbium or yttrium and compounds thereof such as dysprosium sulfate, erbium sulfate, europium oxide, europium sulfate, gadolinium oxide, gadolinium sulfate, holmium oxide, samarium sulfate, terbium oxide, terbium sulfate, thulium oxide, ytterbium sulfide, yttrium oxide, yttrium sulfate, yttrium ferrioxide ($Y_3Fe_5O_{12}$), yttrium aluminum oxide ($Y_3Al_5O_{12}$), other dimetallic compounds such as dysprosium-nickel, dysprosium-cobalt, gadolinium-iron, ytterbium-iron, cobalt-samarium, gadolinium-yttrium, and dysprosium-gallium, and actinide series elements and compounds thereof.

Metal containing-organic molecules useful for the application described above, comprise particles of iron-dextrans such as FeOOH-dextran complexes and other dextran metal complexes wherein the metal is selected from the group comprising cobalt, iron, zinc, chromium, nickel, gallium, platinum, manganese and rare earth metals such as dysprosium, erbium, europium, gadolinium, holmium, samarium, terbium, thulium, ytterbium and yttrium, other dimetallic compounds such as dysprosium-nickel, dysprosium-cobalt, gadolinium-iron, ytterbium-iron, cobalt-samarium, gadolinium-yttrium, and dysprosium-gallium and iron such as $Fe_2O_3$ particles, $Fe_3O_4$ particles and FeOOH particles and $Fe_2O_3$-dextran complexes, $Fe_3O_4$-dextran complexes, and FeOOH dextran complexes, and actinide series elements and. compounds, ferric ammonium citrate, and various iron transporting and chelating compounds such as enterochelin, transferrin, metallothionein, hydroxamates, phenolates, ferrichromes, desferri-ferrichromes, ferritin, ferric mycobactins and iron-sulfur proteins such as ferredoxin and rubredoxin and transferrin as well as transferrin compounds and complexes.

Particularly appropriate metal-containing organic structures for use with the present invention are the porphyrins such as etioporphyrins, mesoporphyrins, uroporphyrins, coproprophyrins, protoporphyrins, and dicarboxylic acid containing prophyrins and substituted prophyrins such as tetraphenylporphyrin sulfonate (TPPS). Especially advantageous protoporphyrins comprise hematoporphyrins, chlorophylls, and cytochromes. In addition to the naturally occurring protoporphyrins which possess either iron or magnesium containing moieties, mixed-metal or di-metal hybrid prophyrins may also be prepared. For example, by substituting an alternative metal for the iron in hematoporphyrin, the advantages of the porphyrin moiety (e.g., in terms of specificity of localization is retained while the unique magnetic properties of the new metal enhance the sensitivity of the substituted molecule. Suitable metals for purposes of substitution comprise cobalt, iron, manganese, zinc, chromium, gallium, nickel, platinum and rare earth series of metals such as dysprosium, erbium, europium, gadolinium, holmium, samarium, terbium, thulium, ytterbium and ytterium, dimetallic compounds such as dysprosium-nickel, dysprosium-cobalt, gadolinium-iron, ytterbium-iron, cobalt-samarium, gadolinium-yttrium, dysprosium-gallium and actinide series elements and compounds thereof. The substituted porphyrins are then optionally reacted with dextran to form a metal-containing porphyrin dextran complex in particle form. Suitable porphyrin acceptors comprise any dicarboxylic acid containing prophyrin such as protoporphyrins (e.g., hematoporphyrins) and the like.

The substitution reaction is carried out in vitro by reacting the desired metal with the desired porphyrin in the presence of the enzyme ferrochelatase (E.C. 4.11.1.1). Reaction conditions as described by Jones and Jones (Biochem. J. 113:507–14, 1969) or Honeybourne, et al. (FEBS Lett.: 98:207–10, 1979) are suitable.

Additional particle systems particularly suited to use in this present invention include $Fe_3O_4$-transferrin dextran, metal-transferrin (transition, rare-earth), metalloporphyrin-transferrin, antibody-ferritin-particles, antibody-ferritin-transferrin particles, antibody-transferrin particles, metal -porphyrin-metal complexes, metallothionein particles, and lectin particles. Useful particle systems for use in this present invention further comprise: Where particle=$Fe_3O_4$, transition metal, rare-earth metal, metalloporphyrin, etc. as well as ferromagnetic and paramagnetic particles.

One magnetic characteristic known to be temperature dependent is magnetic susceptibility. Magnetic susceptibility is measured by the ratio of the intensity of magnetization produced in a substance to the magnetizing force or intensity of the field to which it is subjected. This magnetic characteristic is routinely measured by magnetometer devices such as a vibrating magnetometer or a flux gate magnetometer. Therefore, by measuring the magnetic susceptibility of particles at various temperatures, it is quite simple to calibrate the magnetometer equipment so that when it measures the magnetic susceptibility of the particles a simple calibration will indicate the exact corresponding temperature of the particle.

By way of illustrating the increased magnetic susceptibility of some of the elements or compounds described above, the following table is provided:

| Element or Compound | Temp (K) | Mag.Sus.($10^6$ cgs) |
|---|---|---|
| Iron Oxide (ref.) | 293 | +7,200 |
| Dysprosium Oxide | 287.2 | +89,600 |
| Dysprosium Sulfate Octahydrate | 291.2 | +92,760 |
| Erbium Oxide | 286 | +73,920 |
| Erbium Sulfate Octahydrate | 293 | +74,600 |
| Europium | 293 | +34,000 |
| Europium Oxide | 298 | +10,100 |
| Europium Sulfate | 293 | +25,730 |
| Holmium Oxide | 293 | +88,100 |
| Holmium Sulfate Octahydrate | 293 | +91,600 |
| Terbium | 273 | +146,000 |
| Terbium Oxide | 288.1 | +78,340 |
| Terbium Sulfate Octahydrate | 293 | +76,500 |
| Thulium | 291 | +25,500 |
| Thulium | 296.5 | +51,444 |
| Ytterbium Sulfide | 292 | +18,300 |

Thus, the enhanced magnetic characteristics displayed by the particles of the subject invention results in an increase in an electromagnetic field thereby increasing the overall sensitivity and control of the modalities for the improvement of the instant invention techniques and for the resultant effects.

Magnetic susceptibility has also been used heretofore in connection with the treatment protocol as disclosed in U.S. Pat. No. 4,163,683 of the same inventor, where magnetic susceptibility measurements are correlated with temperature (an interdependent variable) in accomplishing the related induction heating step controllably. There is no recognition, however, that the values for magnetic susceptibility, independent of the induction heating step or the imposition of an electromagnetic field can be usefully correlated (to maximization of particle concentration with time to optimize treatment effectiveness, as demonstrated herein.

A further benefit is derived from the fact that some particle compositions comprise a ferromagnetic, paramagnetic, or diamagnetic component integrated into a cell or organelle specific molecular structure, thereby permitting efficient targeting and delivery of said particles to specific intracellular compartments such as mitochondria, chloroplasts, nuclei, vacuoles, and the like.

This present invention is also applicable to be used in the treatment of atherosclerotic lesions. Descriptions of various aspects of treatment for atherosclerotic lesions is disclosed in U.S. Pat. No. 4,359,453 of the same inventor, incorporated herein by reference.

Further application of this present invention includes the treatment of disease processes, including infectious diseases and organisms comprising Salmonella, Kelbsiclla, Escherichia, Clostridium, Mycobacterium, Pseudomonas, Peptostreptococcus, Phycomyces, Candida, Ustilago, Entamocba, Trypanosoma, Leishmania and RNA viruses. Descriptions of various aspects of treatment for the above described is disclosed in copending and commonly assigned application Ser. Nos. 464,870; 468,644; and 524,844 of the same inventor, incorporated herein by reference.

Thus the invention deals with the use of intracellular particles to enhance the ability to treat infectious diseases. These effects include changes in the cell membrane, receptor sites and interaction with cellular components i.e. mitochondria. It is clear that an effect on the cell membrane and its interrelationship with the mitochondria and the state of energy metabolism in the cell will affect the ability of the cell to resist an infectious agent.

In regard to the aforesaid treatment of infectious diseases, the changes in cell membrane receptors sites and interaction with cellular components, i.e. mitochondria, are also clear. Alterations in any of these processes will affect the eneregy level and metabolic rate in the cell and will easily affect the ability of the cell to resist infectious agents. As an example, the membranes of many bacteria release siderophores which gather iron essential to the bacteria's metabolism. Alteration of membrane events affects the ability of the bacteria to gather the iron and hence affects their metabolism. Similarly, trypanosomes alter the transferrin receptors on cells in number and quality and alters the cell's ability to change energy levels and to resist infection. Therefore by interacting with the cell membrane receptors, one can control the ability of the trypanosomes to survive. Hence, membrane events can control the outcome of infectious disease process.

In addition, particle systems which are kept outside the cell may be utilized to alter membrane events and affect the frequency of response and the energy transmission of the cancer cells and the normal cells In certain circumstances these particles may be utilized to stabilize the membrane of normal cells and decrease their response to a field at a given frequency.

A steady magnetic or electric field may be used to enhance the uptake of particles by the cells as well as enhancing the membrane and cytoplasmic alterations which occur and are fully disclosed and described in copending and commonly assigned application Ser. No. 535,390 of the same inventor incorporated herein by reference. For Example, the application of the localized static mangetic or electric field may occur concurrently with the application of an alternating, oscillating or pulsed electromagnetic field. That is to say, the localized static magnetic or electric field may be superimposed on the subject of interest while the alternating, oscillating or pulsed field is also being applied.

Genetic Engineering processes and DNA-RNA modifications may also be affected and enhanced by the processes described in this present invention. Descriptions of aspects of treatment for the above described in disclosed in copending and commonly assigned application Ser. No. 418,298 of the same inventor incorporated herein by reference.

These modification include changes in conformation, structure, alteration in binding sites and changes in histone binding. All of these modifications will affect the genetic engineering process. As an example; when a portion of nucleic acid is introduced into a strand of DNA, the conformation and binding sites available on the DNA greatly influence whether the nucleic acid is able to join the DNA. The exact modification depends on the desired result.

Further with regard to DNA, RNA modifications, the fact that changes in conformation, structure, alteration in binding sites and changes in histone binding will affect the function of DNA-RNA interactions is well-known to those "skilled in the art." The binding of DNA or nucleic acids to histones and proteins greatly affects the ability of the DNA to be functionally active as well as to affect its conformation.

Ultrasound mechanisms may also be affected by the processes described in this present invention to enhance the differentiation techniques. This is evidenced by the attenuation of ultrasound energy in particle systems similiar to iron porphyrin $FeTPPS_4$ i.e. (Hemoglobin). The orientation of the tissue is also important and can be utilized to maximize the effect of the E field or the H field.

Temperature measurements are taken in living tissue of the host organism and correlating the temperature readings to the low frequency magnetic field causing alteration in dielectric properties and/or conductivity and/or frequency dependent dispersion curves. Once the temperature is correlated with these measurements, (dielectric properties, conductivity and frequency dependent dispersion curves) these measurements are then made along three axes at right angles to one another in the host organism from which a three dimensional temperature map of the body is produced by restructuring them in a three dimensional temperature model by computer processes well known in the art.

The frequency of the magnetic field is selected to enhance the dielectric properties, conductivity and electric dipoles of the cells of the host organism and will vary depending upon the particles employed in the host. The frequency, however, is adjusted so that thermal effects thereby obtained are not due to hysteresis loss from the particles themselves but rather the alteration in conductibility, dielectric properties and electric dipoles of the cells that are brought about by the use of the particles of the present invention. Generally, the range of frequencies that may be employed will be anywhere from about 1 hz to about 500 MHz; 1 Hz to about 100 MHz; 1 Hz to less than 13 MHz; 1 Hz to about 100 KHZ; 1 hertz up to less than 50 kilohertz and especially from about 10 hertz up to about less than 50 kilohertz as well as any frequency within these ranges or range of frequencies within the aforesaid ranges.

The present invention, therefore, will be practiced at the above frequencies and the copending applications incorporated herein by reference will give the person of ordinary skill in the art a disclosure of how to practice the present invention with the exception that the frequencies described above will be employed in lieu of those utilized in such copending applications.

To further illustrate the operation of the subject procedure, the following treatment scenario is provided.

Reference herein to tissue, organ or cell population is intended in its most embracive and comprehensive sense, referring in general to the region of the host organism affected by the invasive abnormality, or the treatment region, as the context requires.

The subject receives an intravenous injection of a colloidally suspended particle such as iron porphyrin ($FeTPPS_4$) at a dosage of 2-10 mg/kg. After 48 hours, the subject is exposed to an alternating electromagnetic field at a frequency of 1 Hz to 100 MHz in this case 500 Hz for a period of approximately 10-20 minutes. The alternating electromagnetic field may be applied via a coil arrangement or via capacitor plates or via electrodes in the tissue or any suitable means available in the state of the art, and consistent in application to this present invention. The process may be repeated as is necessary.

In summary, the introduction and absorption of minute particles into the cell alters the intracellular environment and the charge accumulation on the membrane. Consequently, lower power levels may be used to transmit energy into the cell, lower frequencies may be used because of the alteration in membrane events and the effect on normal cells is greatly reduced because of the above as well as the state of the normal cell's membrane. In addition, modification can be performed by using particles to alter the extracellular environment as well.

In addition, since radiofrequency fields can affect particles by causing reversible or irreversible changes in the particles, i.e. magnetostrictive induced vibrations, by affecting the particles with an alternating electromagnetic field in the range 1 Hz to 500 MHz either prior or during treatment, the particles can be made more or less responsive to the field. This alternating field can produce acoustic changes in the particle and affect the cell and subcellular structures.

What is claimed is:

1. A process for the treatment of diseased cells in at least one region in the tissue of a host organism containing said diseased cells and living normal cells without substantially damaging said living normal cells comprising:

providing to said host organism minute particles less than about 1 micron capable of being taken up by said diseased cells;

selecting said particles to affect intracellular and extracellular events for the enhancement of treating infectious diseases produced by organisms selected from the group consisting of Salmonella, Klebsiella, Escherichia, Clostridium Mycobacterium, Pseudomonas, Peptostreptococcus, Phycomyces, Candida, Ustilago, Entamoeba, Trypanosoma, Leishmania and RNA viruses by the selection of said particles;

allowing said particles to effect at least one event comprising intracellular events and membrane events in said tissue;

subjecting said organism to a relatively low frequency alternating, oscillating, or pulsed electromagnetic field to provide energy to said diseased cells and selectively heat said diseased cells wherein said particles are selected from the group consisting of:
a) cobalt, zinc, iron, chromium, nickel, platinum, rare earth metals and compounds selected from the group consisting of dysprosium, erbium, europium, gadolinium, holmium, samarium, terbium, thulium, ytterbium, yttrium; dysprosium sulfate, erbium sulfate, europium oxide, europium sulfate, gadolinium oxide, gadolinium sulfate, holmium oxide, samarium sulfate, terbium sulfate, thulium oxide, ytterbium sulfide, yttrium oxide, yttrium sulfate, yttrium ferrioxide ($Y_3Fe_5O_{12}$), yttrium oxide ($Y_3Al_5O_{12}$), dysprosium-nickel, dysprosium-cobalt, gadolinium-iron, ytterbium-iron, cobalt-samarium, gadolinium-ytterbium, dysprosium-gallium, and actinide series elements and compounds thereof;
b) dextran metal complexes wherein said metal is selected from the group consisting of cobalt, zinc, chromium, iron, gallium, manganese, nickel, platinum, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium, gadolinium-yttrium, and dysprosium-gallium;
c) iron transporting and chelating compounds selected from the group consisting of ferric ammonium citrate, enterochelin, transferrin, metallothionein, hydroxamates, phenolates, ferrichromes, desferriferrichromes, ferritin, ferric mycobactins, ferredoxin and rubredoxin;
d) porphyrins selected from the group consisting of etioporphyrins, meso-porphyrins, uroporphyrins, coproporphyrins, protoporphyrins, dicarboxylic acid containing porphyrins, tetraphenylporphyrin sulfonate, hematoporphyrins, chlorophylls, and cytochromes;
e) and combinations of the materials of said sub-paragraphs a), b), c) and d).

2. A process comprising selecting particles of less than about 1 micron to affect intracellular and extracellular events for the enhancement of Genetic Engineering processes or for DNA-RNA modifications by the selection of said particles comprising, introducing said particles into a host organism and subjecting said host organism to a relatively low frequency alternating, oscilating or pulsed electromagnetic field to provide energy to said organism and enhance said Genetic Engineering process wherein said particles are selected from the group consisting of:
a) cobalt, zinc, iron, chromium, nickel, platinum, rare earth metals and compounds selected from the group consisting of dysprosium, erbium, europium, gadolinium, holmium, samarium, terbium, thulium, ytterbium, yttrium; dysprosium sulfate, erbium sulfate, europium oxide, europium sulfate, gadolinium oxide, gadolinium sulfate, holmium oxide, samarium sulfate, terbium sulfate, thulium oxide, ytterbium sulfide, yttrium oxide, yttrium sulfate, yttrium ferrioxide ($Y_3Fe_5O_{12}$), yttrium oxide ($Y_3Al_5O_{12}$), dysprosium-nickel, dysprosium-cobalt, gadolinium-iron, ytterbium-iron, cobalt-samarium, gadolinium-ytterbium, dysprosium-gallium, and actinide series elements and compounds thereof;
b) dextran metal complexes wherein said metal is selected from the group consisting of cobalt, zinc, chromium, iron, gallium, manganese, nickel, platinum, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium; gadolinium-yttrium, and dysprosium-gallium, $Fe_3O_4$ $Fe_2O_3$, $Fe_2O_3$, FeOOH:
c) iron transporting and chelating compounds selected from the group consisting of ferric ammonium citrate, enterochelin, transferrin, metallothionein, hydroxamates, phenolates, ferrichromes, desferriferrichromes, ferritin, ferric mycobactins, ferredoxin and rubredoxin;
d) porphyrins selected from the group consisting of etioporphyrins, meso-porphyrins, uroporphyrins, coproporphyrins, protoporphyrins, dicarboxylic acid containing porphyrins, tetraphenylporphyrin sulfonate, hematoporphyrins, chlorophylls, and cytochromes;
e) and combinations of the materials of said sub-paragraphs a), b), c) and d).

3. A process for the treatment of diseased cells in at least one region in the tissue of a host organism containing said diseased cells and living normal cells without substantially damaging said living normal cells comprising:
providing to said host organism minute particles less than about 1 micron capable of being taken up by said diseased cells;
selecting said particles to affect intracellular and extracellular events for the enhancement of treating infectious diseases produced by organisms selected from the group consisting of Salmonella, Klebsiella, Escherichia, Clostrididium, Mycobacterium, Pseudomonas, Peptostreptococcus, Phycomyces, Candida, Ustilago, Entamoeba, Trypanosoma, Leishmania and RNA viruses by the selection of said particles;
allowing said particles to effect at least one event comprising intracellular events and membrane events in said tissue;
subjecting said organism to a relatively low frequency alternating, oscillating, or pulsed electromagnetic field to provide energy to said diseased cells and selectively heat said diseased cells wherein said particles are selected from the group consisting of:
a) ferromagnetic, paramagnetic and diamagnetic elements, inorganic compounds, organic compounds and combinations thereof,metalloporphyrins, $Fe_2O_3$, FeOOH, and metal metalloporphyrins.

4. A process comprising selecting particles of less than about 1 micron to affect intracellular and extracellular events for the enhancement of Genetic Engineering processes or for DNA-RNA modifications by the selection of said particles comprising, introducing said particles into a host organism and subjecting said host organism to a relatively low frequency alternating, oscillating or pulsed electromagnetic field to provide energy to said organism and enhance said Genetic Engineering process wherein said particles are selected from the group consisting of:
a) paramagnetic and diamagnetic elements, inorganic compounds, organic compounds and combinations thereof, metalloporphyrins, $Fe_2O_3$, FeOOH, and metal metalloporphyrins.

5. The process of claims 1, 2, 3 or 4 wherein said alternating, oscillating and/or pulsed electromagnetic field is between about 1 Hz to about 100 MHz.

6. The process of claims 1, 2, 3, or 4 wherein said alternating, oscillating and/or pulsed electromagnetic field is produced by apparatus comprising a coil, capacitor plates or electrodes in the said host organism.

7. The process of claims 1, 2, 3 or 4 wherein said particles are selected to affect the intracellular conductivity, dielectric properties, charge accumulation on the membrane, membrane conductance, membrane capacitance and the electric dipole environment of cells.

8. The process of claims 1, 2, 3 or 4 wherein the natural occurring metal moiety of said porphyrin is optionally substituted with a metal selected from the group comprising cobalt, zinc, chromium, gallium, iron, manganese, nickel, platinum, dyprosium, erbium, europium, gadolinium, holmium, samarium, terbium, thulium, ytterbium, yttrium, dyprosium-nickel, dyprosium-cobalt, gadolinium-iron, yttrebium-iron, cobalt-samarium, gadolinium-yttrium, and dyprosium-gallium; and combinations thereof.

9. The process according to claims 1, 2, 3 or 4 wherein said iron transporting, iron chelating and porphyrin compounds are chemically complexed with dextran.

10. The process according to claims 1, 2, 3 or 4 wherein said compound is chemically complexed with an antibody.

11. The process of claims 1, 2, 3 or 4 for heating said host organism comprising decreasing the power level at a given frequency of said field by altering intracellular environment and membrane characteristics in said tissue by the provision of said particles to said host.

12. The process of claims 1, 2, 3 or 4 for heating said diseased cells comprising decreasing the frequency of said field by altering the intracellular environment and membrane characteristics in said tissue by the provision of said particles to said host.

13. The process of claims 1, 2, 3 or 4 comprising applying a localized static magnetic field to said host organism to aid in the intracellular uptake and energy absorption of the electric or magnetic dipoles either introduced or already present in said host organism.

14. The process of claims 1, 2, 3 or 4 wherein a localized static magnetic or electric filed is applied to said host organism after providing said particles to said host organisms but prior to or during the application of said alternating, oscillating and/or pulsed electromagnetic field to enhance the intracellular of energy and the energy-absorption responsiveness of said particles.

15. The process of claim 13 wherein a localized static magnetic or electric field is applied to said host organism prior to and/or during the application of said alternating, oscillating and/or pulsed electromagnetic field to enhance the intracellular energy uptake and energy absorption of the electric or magnetic dipoles either introduced or already present in said tissue.

16. The process of claim 13 wherein the static magnetic or electrical field is between 100 gauss and 80 kilogauss.

17. The process of claims 1 or 3 wherein said particles are introduced into the extracellular environment of said tissue to alter membrane events and potentiate energy delivery to said diseased cells and/or reduce energy delivery to said normal cells.

18. The process of claims 1 or 3 wherein particles are introduced intravenously, intra-arterially, intra-lymphatically, and or locally.

19. The process of claims 1, 2, 3 or 4 wherein an alternating electromagnetic filed between 1 Hz and 500 MHz is used to affect said particles and make them more or less responsive to an exciting alternating electromagnetic field produced by magnetostrictive induced vibrations applied to said host organism.

* * * * *

UNITED STATES PATENT AND TRADEMARK OFFICE
CERTIFICATE OF CORRECTION

PATENT NO. : 5,087,438

DATED : February 11, 1992

INVENTOR(S) : Robert T. Gordon

It is certified that error appears in the above-identified patent and that said Letters Patent is hereby corrected as shown below:

Column 3, line 60: "benefits" should read as --benefits.--

Column 8, line 1: "concentration" should read as --concentration)--

Column 12, line 9, Claim 2: delete second occurrence of --$Fe_2O_3$,--

Column 14, line 9, Claim 14: "filed" should read as --field--

Column 14, line 25, Claim 17: delete --said--

Column 14, line 32, Claim 18: "and or" should read as --and/or--

Column 14, line 34, Claim 19: "filed" should read as --field--

Signed and Sealed this

Thirty-first Day of August, 1993

Attest:

*Attesting Officer*

BRUCE LEHMAN

*Commissioner of Patents and Trademarks*